US008827698B2

(12) United States Patent
Lai et al.

(10) Patent No.: US 8,827,698 B2
(45) Date of Patent: Sep. 9, 2014

(54) ORTHODONTIC APPLIANCE WITH LOW PROFILE CLIP

(75) Inventors: Ming-Lai Lai, Arcadia, CA (US); Ralf Schlimper, Melle (DE); Sunghan Kim, Montebello, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/498,408

(22) PCT Filed: Oct. 20, 2010

(86) PCT No.: PCT/US2010/053347
§ 371 (c)(1),
(2), (4) Date: Mar. 27, 2012

(87) PCT Pub. No.: WO2011/068601
PCT Pub. Date: Jun. 9, 2011

(65) Prior Publication Data
US 2012/0231408 A1   Sep. 13, 2012

Related U.S. Application Data

(60) Provisional application No. 61/265,854, filed on Dec. 2, 2009.

(51) Int. Cl.
A61C 3/00 (2006.01)
A61C 7/30 (2006.01)
A61C 7/14 (2006.01)

(52) U.S. Cl.
CPC . *A61C 7/30* (2013.01); *A61C 7/148* (2013.01); *A61C 7/145* (2013.01)
USPC .......................................... 433/11

(58) Field of Classification Search
USPC ....................................... 433/8–24
See application file for complete search history.

(56) References Cited

U.S. PATENT DOCUMENTS

| 5,595,484 A * | 1/1997 | Orikasa et al. ............ 433/8 |
| 6,302,688 B1 * | 10/2001 | Jordan et al. ............ 433/8 |
| 6,554,612 B2 * | 4/2003 | Georgakis et al. ........ 433/11 |

(Continued)

FOREIGN PATENT DOCUMENTS

| WO | 2007/141226 | 12/2007 |
| WO | 2010/014299 | 2/2010 |

(Continued)

OTHER PUBLICATIONS

International Search Report PCT/US2010/053347 Apr. 15, 2011, 5 pgs.

*Primary Examiner* — Cris L Rodriguez
*Assistant Examiner* — Mirayda A Aponte
(74) *Attorney, Agent, or Firm* — Kevin W. Weber

(57) ABSTRACT

Provided is an improved self-ligating orthodontic appliance and methods of assembling the same. The improved orthodontic appliance uses at least one resilient clip to releasably couple an archwire to the body, where a portion of the clip is rigidly coupled to the appliance body in a position and orientation that minimizes the overall profile of the appliance. The appliance is assembled by combining a press fit coupling between the clip and appliance body with an interference fit coupling between the clip and retaining structure located on the body. Advantages include a greater freedom to select a bonding pad location, lower bracket profile, decreased engagement force, enhanced clip fatigue life, and ease of assembly.

20 Claims, 14 Drawing Sheets

(56) References Cited

U.S. PATENT DOCUMENTS

| | | | |
|---|---|---|---|
| 6,582,226 B2* | 6/2003 | Jordan et al. | 433/10 |
| 6,663,385 B2* | 12/2003 | Tepper | 433/11 |
| 6,776,614 B2 | 8/2004 | Wiechmann | |
| 7,063,531 B2* | 6/2006 | Maijer et al. | 433/11 |
| 7,140,876 B2* | 11/2006 | Cinader et al. | 433/10 |
| 7,217,125 B2* | 5/2007 | Lai et al. | 433/11 |
| 7,252,505 B2* | 8/2007 | Lai | 433/11 |
| 7,367,800 B2* | 5/2008 | Lai et al. | 433/11 |
| 7,377,777 B2* | 5/2008 | Lai et al. | 433/11 |
| 8,147,243 B2* | 4/2012 | Wiechmann | 433/9 |
| 2005/0095549 A1* | 5/2005 | Cinader et al. | 433/10 |
| 2006/0014116 A1* | 1/2006 | Maijer et al. | 433/11 |
| 2006/0024635 A1* | 2/2006 | Lai | 433/11 |
| 2006/0147868 A1* | 7/2006 | Lai et al. | 433/11 |
| 2006/0172249 A1* | 8/2006 | Lai et al. | 433/11 |
| 2007/0072143 A1* | 3/2007 | Sommer | 433/10 |
| 2010/0003631 A1 | 1/2010 | Wiechmann | |
| 2011/0143301 A1* | 6/2011 | Maijer et al. | 433/11 |
| 2012/0028207 A1* | 2/2012 | Cleary et al. | 433/10 |
| 2012/0183917 A1* | 7/2012 | Wiechmann | 433/24 |

FOREIGN PATENT DOCUMENTS

| | | |
|---|---|---|
| WO | 2010/014518 | 2/2010 |
| WO | WO 2010014299 A1 * | 2/2010 |
| WO | WO 2010014518 A2 * | 2/2010 |

* cited by examiner

ORTHODONTIC APPLIANCE WITH LOW PROFILE CLIP

CROSS REFERENCE TO RELATED APPLICATIONS

This application is a national stage filing under 35 U.S.C. 371 of PCT/US2010/053347, filed Oct. 20, 2010, which claims priority to U.S. Provisional Application No. 61/265,854, filed Dec. 2, 2009, the disclosure of which is incorporated by reference in their entirety herein.

TECHNICAL FIELD

Intraoral appliances and related methods are provided for use during the course of orthodontic treatment. More specifically, self-ligating intraoral appliances and related methods are provided that use one or more clips to releasably retain an archwire in an archwire slot of the respective appliance during orthodontic treatment.

BACKGROUND ART

Orthodontic therapy is a specialty of dentistry that involves diagnosis and treatment of a malocclusion (or improper bite) to reposition teeth to proper locations in the oral cavity. Orthodontic therapy often enhances the aesthetic appearance of the teeth, especially in instances when the patient's front teeth are crooked. Orthodontic treatment can also improve the patient's bite, or occlusion, so that the upper and lower teeth are better coordinated with each other when the patient is chewing.

A common type of orthodontic treatment involves a set of intraoral appliances that are often collectively called "braces". In this type of treatment, slotted appliances called brackets are initially bonded to the patient's anterior, cuspid and bicuspid teeth and tubular appliances called buccal tubes are bonded to the patient's molar teeth. After bonding these appliances to the teeth, a resilient appliance called an archwire is secured in the slot of each bracket, and the ends of the archwire anchored in the buccal tubes. During treatment, the archwire imparts forces to the teeth and also forms a track thereby guiding movement of the teeth to desired positions.

Many orthodontic brackets have lugs known as "tiewings" that are connected to a body of the bracket. Once the bracket has been attached to a tooth and an archwire has been placed in the archwire slot of the bracket, a ligature is coupled to the bracket with assistance of these tiewings to retain the archwire in the archwire slot. One example of a commercially available orthodontic ligature is a small, elastomeric O-ring that is installed by stretching the O-ring along a path behind the tiewings and over the facial side of the archwire.

Other types of orthodontic appliances called self-ligating appliances have a latch for coupling the archwire to the bracket. Use of the latch conveniently avoids the need to use ligatures to secure the archwire to the appliance. The latch may comprise a movable clip, spring member, sliding cover, shutter, bail or other structure that is connected to the appliance body for retaining the archwire in the archwire slot. Compared with traditional ligated appliances, self-ligating appliances can reduce friction between the archwire and the archwire slot during treatment, which can be advantageous in facilitating tooth movement.

Examples of improved, self-ligating orthodontic appliances with clips are described in U.S. Pat. No. 6,582,226 (Jordan et al.), U.S. Pat. No. 7,140,876 (Cinader et al.), U.S. Pat. No. 7,217,125 (Lai et al.), U.S. Pat. No. 7,377,777 (Lai et al.), and PCT Publication No. WO2010/014518 (Lai et al.). The appliances described in those documents have one or more clips for retaining an archwire in the archwire slot, and the clips release the archwire from the archwire slot whenever the archwire exerts a force on the appliance that exceeds a certain minimum value. The minimum value is significantly less than the force required in the same direction to debond the appliance from the tooth, and consequently helps to ensure that the appliance will not spontaneously debond from the tooth during the course of treatment.

SUMMARY

Orthodontic appliances having an overall, generally small (or low) profile are often desired by practitioners for use in treatment. Such low profile appliances are less likely to contact other teeth or appliances in the patient's oral cavity, an important advantage in certain instances when the teeth are not initially positioned in substantial alignment relative to each other. Low profile appliances are also less likely to impinge on the patient's oral tissue and cause irritation to the patient. Additionally, low profile appliances have the potential to be more hygienic, because there are smaller or fewer areas where food particles and plaque may accumulate during the course of treatment.

The advantages of low profile appliances are even greater when dealing with lingual braces, in which appliances are bonded to the lingual (or tongue-side) of the teeth. Because of the concavity of the dental arch and the need to accommodate the tongue, the amount of space for appliances is far more limited on the lingual side of the teeth than on the facial side of the teeth. Additionally the treatment mechanics on the lingual side of the teeth generally benefit from having a sufficient distance between neighboring appliances, known as inter-bracket spacing. Inter-bracket spacing is inversely related to the profile of the appliances, thus providing another incentive to decrease appliance profile with lingual braces.

Disclosed herein is an improved self-ligating orthodontic appliance and methods of assembling the same. This improved orthodontic appliance uses at least one resilient clip aligned with an archwire slot in a bracket body to releasably couple an archwire to the body. A portion of the clip is rigidly coupled to the appliance body in a position and orientation that minimizes the overall profile of the appliance. The appliance is assembled by combining a press fit coupling between the clip and appliance body with an interference fit coupling between the clip and retaining structure located on the body.

The improved appliance provides one or more advantages over prior art configurations. First, the shape and profile of the appliance provides a practitioner and/or manufacturer greater freedom to select a bonding pad location on the lingual side of a tooth. Second, each clip has only a single prong, which allows for decreased engagement force and improved patient comfort. Third, the relative positioning of the clip and the body provides extra space for clip deflection, thereby distributing the strain on the clip and extending clip fatigue life. Moreover, the configuration of this appliance leverages the flexibility of the clip in its method of manufacture. Advantageously, there is no need to weld, braze or adhesively attach the clip to the appliance body.

The clip has a generally "J"-shaped configuration and can be oriented so that it deflects either toward or away from the bonding pad when receiving an archwire. In some configurations, the terminal end of the clip extends beyond the edge of the bracket body on the opposite side of the archwire slot, allowing an archwire to engage a side wall of the archwire slot in directions parallel to the slot bottom. Advantageously, this configuration allows archwire alignment and archwire engagement to be conveniently decoupled into two separate steps, making ligation simpler for the practitioner. This configuration also enables the bracket body to be made smaller, resulting in an even lower profile appliance.

In one aspect, a self-ligating orthodontic appliance is provided. The self-ligating appliance comprises a base having an outer surface for attachment to a tooth and an inner surface; a body extending outwardly from the inner surface, the body including a pair of side walls and a bottom wall extending between the side walls in a direction generally perpendicular thereto, wherein the side walls and the bottom wall define an archwire slot extending in a generally mesial-distal direction; and at least one resilient clip adjacent the body for releasably retaining an archwire in the archwire slot, the clip comprising a fixed portion rigidly coupled to the body and a free portion extending outwardly from the fixed portion along a path next to the bottom wall, wherein the pair of side walls defines a pair of reference planes and the fixed and free portions join each other in a location between the reference planes.

In another aspect, a self-ligating orthodontic appliance is provided, comprising a base having an outer surface for attachment to a tooth and an inner surface, a body extending outwardly from the inner surface, the body including a pair of spaced-apart side walls and a bottom wall defining an archwire slot with a slot opening, the archwire slot and the slot opening extending in a generally mesial-distal direction, and wherein the side walls extend in respective reference planes that are generally parallel to each other, and at least one resilient clip adjacent the body for releasably retaining an archwire in the archwire slot, the clip comprising a fixed portion secured to the body in a location adjacent the bottom wall and a free portion extending along a portion of the bottom wall, one of the side walls and the slot opening, wherein the free portion includes a head portion that terminates in a location between the reference planes, and wherein the fixed and free portions join each other in a location between the reference planes.

In still another aspect, a self-ligating orthodontic appliance is provided comprising a base having an outer surface for attachment to a tooth and an inner surface; a body extending outwardly from the inner surface and having an archwire slot thereon extending in a generally mesial-distal direction, the archwire slot having opposing first and second side walls and a bottom wall; and at least one resilient clip coupled to the body for releasably retaining an archwire in the archwire slot, the clip comprising a fixed portion rigidly coupled to the body, and a free portion extending outwardly from the fixed portion along the bottom wall, further extending in a certain direction along the first side wall and terminating beyond the edge of the second side wall in the certain direction when relaxed, thereby presenting a path for the archwire to engage the free portion in a direction opposing the first side wall and generally parallel to the bottom wall.

Also provided is a method of assembling an orthodontic appliance comprising providing a resilient clip having an archwire receiving region, providing a bracket body having an archwire slot extending across one side of the body and a cavity complemental to at least a portion of the clip, positioning the clip next to the cavity such that the archwire receiving region is aligned with the archwire slot, urging the clip toward the cavity to press fit a portion of the clip into the body while deflecting another portion of the clip around a tab located on the body, wherein the tab provides an interference fit to subsequently retain the clip against the body.

Further provided is a method of assembling an orthodontic appliance, comprising providing a resilient clip having an archwire receiving region; providing a body having an archwire slot extending across one side of the body and a cavity complemental to at least a portion of the clip, wherein the cavity has at least one inner wall that is tapered; placing the clip in the cavity such that the archwire receiving region is aligned with the archwire slot; and urging an enlarged broaching tool into the cavity to permanently deform the inner wall of the cavity toward the clip, wherein the deformed inner wall provides an interference fit to retain the clip against the body.

Further provided is a method of ligating a self-ligating orthodontic appliance having an archwire slot with a pair of side walls and a bottom wall and a resilient clip coupled to the body for releasably retaining an archwire in the archwire slot, the method comprising urging the archwire against the clip in a direction generally parallel to the bottom wall to deflect the clip in a direction that provides access to the archwire slot; and moving the archwire in a direction generally parallel to the side walls to seat the archwire within the archwire slot and allow the clip to return toward a relaxed configuration to retain the archwire.

DEFINITIONS

Figure 1:
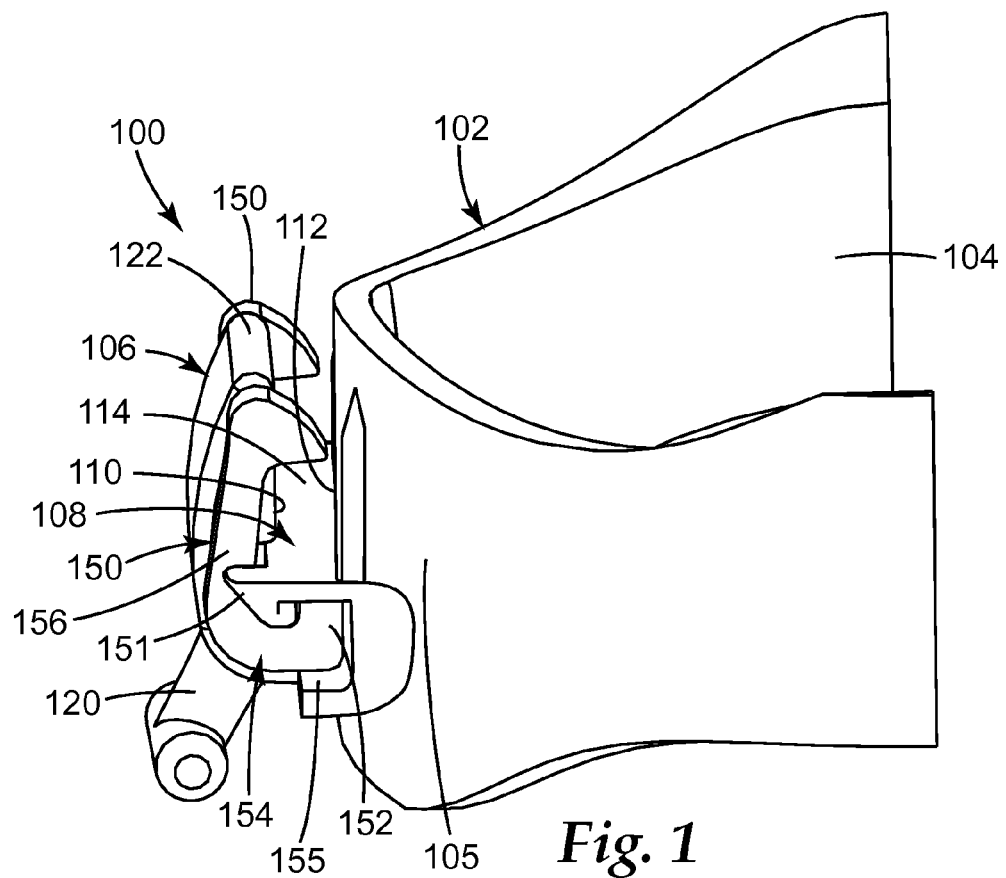
FIG. 1 is a perspective view of an assembled self-ligating orthodontic appliance according to one embodiment, looking at the lingual, mesial, and occlusal sides.

As used herein:

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION

Described herein are self-ligating orthodontic appliances adaptable for attachment to the teeth of a patient and capable of receiving an archwire to impart corrective forces to the teeth. These appliances are preferably a part of a system of appliances that are bonded to some or all of the central, lateral, cuspid, bicuspid, and molar teeth of a dental arch and collectively cooperate with a suitable archwire to guide the teeth to proper locations. This system of appliances is also contemplated for use on both upper and lower arches. It is also to be understood that the system of appliances may be adapted for attachment to either the lingual or labial surfaces of teeth.

These appliances can have particular configurations that vary substantially from tooth to tooth, based for example on differences in the shapes of the respective teeth. The configuration of these appliances may also vary substantially from one patient to another. For example, these appliances can be customized based on the initial and finished arrangements of the teeth unique to a particular patient. It is to be understood that the concepts and principles below can be applied by the skilled artisan to enable a system of self-ligating appliances to be provided for any and all of the aforementioned teeth in the upper and lower dental arches.

FIGS. 1-5 show an exemplary self-ligating orthodontic bracket according to one embodiment in various views. The bracket shown is adapted for attachment to the lingual side of a lower bicuspid tooth and designated herein by the numeral 100. The bracket 100 includes an oversized base 102 having an outer surface 104 adapted for attachment to a respective lower bicuspid tooth (not shown). The outer surface 104 is generally concave as shown and has an overall contour which preferably matches the outer contour of the tooth. If desired, the outer surface 104 may further include a retaining structure that facilitates bonding the bracket 100 directly to a patient's tooth. For example, the retaining structure can improve adhesion by forming a mechanical lock or chemical bond with a suitable adhesive disposed between the outer surface 104 and the tooth surface. Retaining structure may include holes, grooves, particles, recesses, undercuts, a micro-etched surface, a chemical bond enhancement material, or any other structure, material or combination thereof.

As shown in FIGS. 1-5, the base 102 is adapted to extend across a portion of the perimeter of the tooth. Optionally but not shown, the base 102 may fully encircle the tooth, resulting in a banded appliance. Banded appliances are advantageous because the adhesive between the appliance and the tooth extends over a large surface area, providing increased bond reliability compared with non-banded appliances. Banding the bracket 100 may be especially useful in the posterior areas of the mouth, where the aesthetics of the appliance are generally not an issue.

The base 102 also includes an inner surface 105, which is generally convex and is located on the opposite side of the base 102 from the outer surface 104. A bracket body 106 extends outwardly from the inner surface 105 in a generally lingual direction. In some embodiments, the body 106 is integral with the base 102. The body 106 further includes an archwire slot 108 having a first side wall 110, a second side wall 112, and a bottom wall 114 extending between, and perpendicular to, the side walls 110,112, thereby presenting a slot opening. The archwire slot 108 and the slot opening extend in a generally mesial-distal direction, while the bottom wall 114 faces a generally occlusal direction. Optionally and as shown, the second side wall 112 is coplanar with the inner surface 105 along a portion of the length of the archwire slot 108. As further shown in FIG. 2, the lingual-facing surfaces of the body 106 have a generally teardrop-shaped contour when viewed in planes perpendicular to the longitudinal axis of the archwire slot 108.

A generally "T"-shaped bracket hook 120 extends from the lingual-gingival side of the body 106. Preferably and as shown, the hook 120 protrudes at a slight angle away from the base 102 to avoid interference with the gingiva when the bracket 100 is bonded to a patient. As shown in the lingual view of the bracket 100 in FIG. 3, the hook 120 is located at the approximate mesial-distal center of the bracket 100. During treatment, the hook 120 can be advantageously coupled to elastics, springs, or other orthodontic auxiliaries as seen fit by the orthodontic practitioner.

Figure 2:
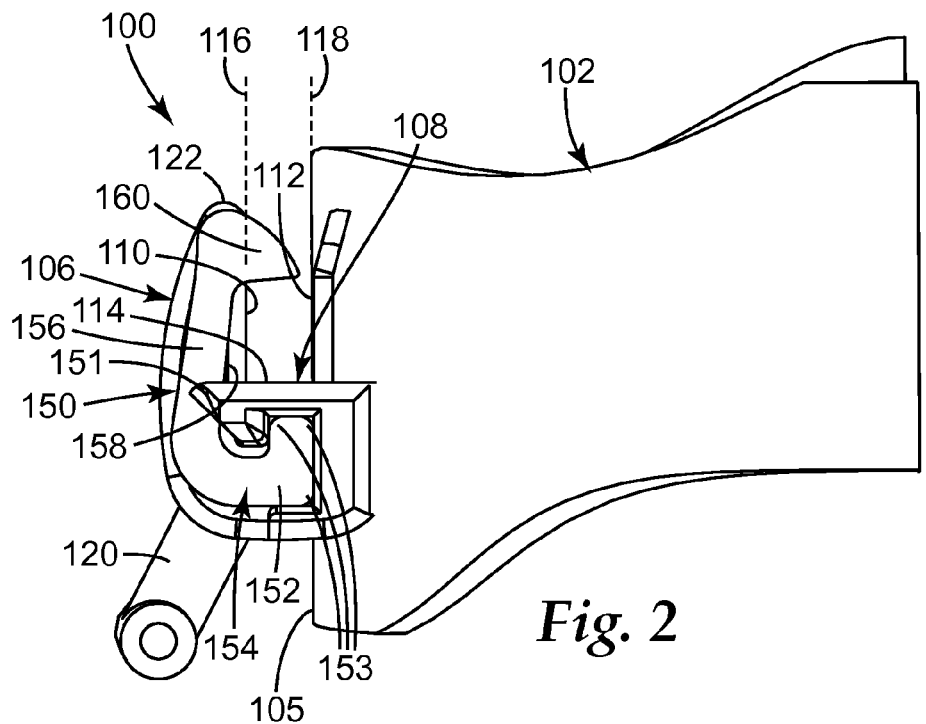
FIG. 2 is mesial view of the appliance in FIG. 1, looking at the mesial side.

A pair of resilient clips 150 are located adjacent the mesial and distal sides of the body 106 and permit the bracket 100 to releasably retain an archwire in the archwire slot 108. As shown in FIGS. 1-2, each clip 150 is planar and has a generally "J"-shaped configuration in plan view. Each clip 150 has a terminal fixed portion 152 that is rigidly coupled to the body 106 in a location adjacent the bottom wall 114. As defined herein, portions of the clip 150 which are "rigidly coupled" to the body 106 are constrained such that they do not substantially move or deflect relative to the body 106. It is understood, however, that manufacturing tolerances may allow for one or more small gaps between the clip 150 and the body 106, and result in a slight relative movement between these elements.

Figure 3:
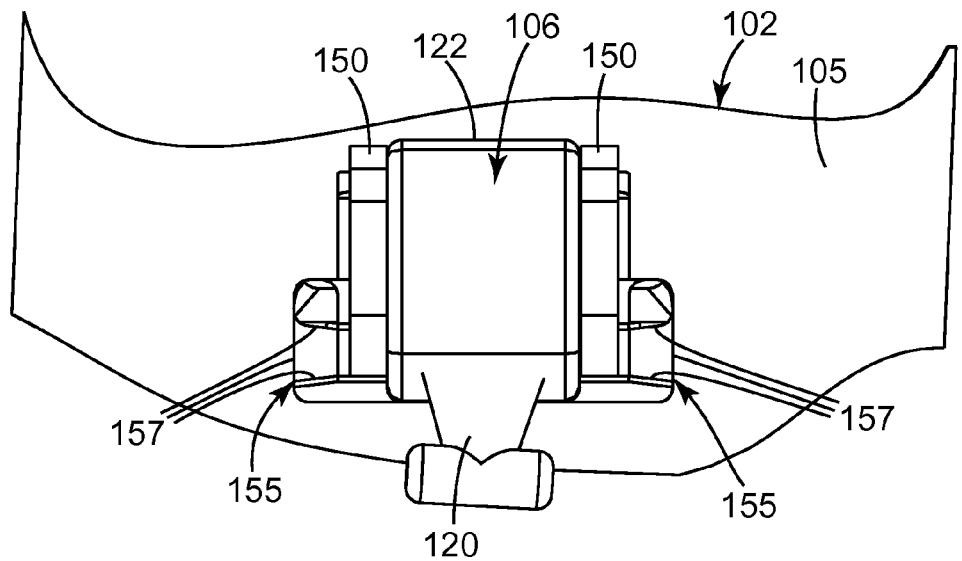
FIG. 3 is a lingual view of the appliance in FIGS. 1-2, looking at the lingual side.

As shown in FIG. 1, the fixed portions 152 of the clips 150 are press fit into open-ended cavities 155 located on the mesial and distal sides of the body 106. Preferably, each cavity 155 has a shape that complemental to at least a portion of the each respective fixed portion 152 such that there is no substantial movement of the fixed portion 152 within the cavity 155. Optionally and as shown in FIG. 2, the fixed portion 152 includes one or more corner regions 153, which further assist in constraining sliding or rotational movement of the fixed portion 152 within the body 106. The clips 150, as shown FIGS. 1 and 3, are also retained against the body 106 by retaining tabs 151, which protrude from the lingual side of the body 106 and extend along at least a portion of each cavity 155. The press-fit coupling in combination with the retaining tabs 151 advantageously prevent the clips 150 from becoming inadvertently dislodged from the body 106 during treatment.

Figure 4:
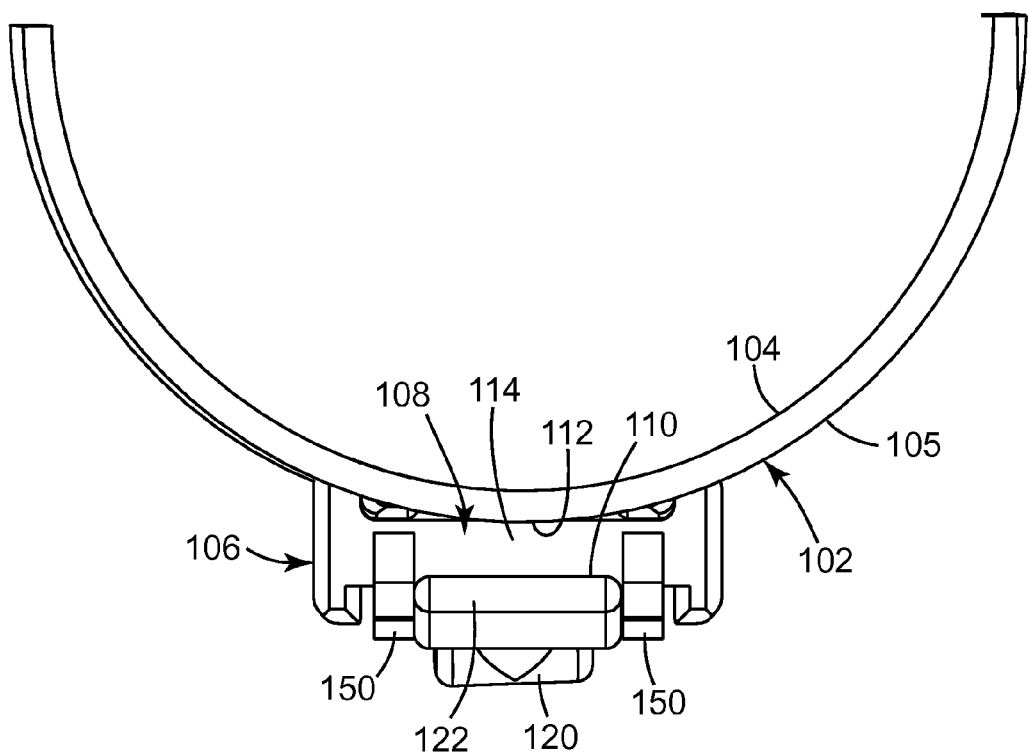
FIG. 4 is an occlusal view of the appliance in FIGS. 1-3, looking at the occlusal side.

Optionally and as shown in FIGS. 3 and 4, the bracket 100 uses a pair of clips 150 which are identical to each other and symmetrically disposed along the mesial and distal sides of the body 106. By using a pair of clips 150, the bracket 100 advantageously provides both a mesial and a distal point of contact with the archwire, thereby improving the practitioner's control over "tipping" movements of the respective tooth (rotational movement about the facial-lingual axis).

Each clip 150 further includes an elongated, curved free portion 154 that is integrally connected to the fixed portion 152 and extends from the fixed portion 152 in a direction away from the base 102 along a path next to the bottom wall 114. As particularly shown in FIG. 2, the pair of side walls 110,112 extend in respective reference planes 116,118 (shown in dashed lines) that are generally parallel to each other and the fixed and free portions 152,154 join each other at a location between the reference planes 116,118.

The free portion 152 further includes an arm portion 156 and a head portion 160. From where the fixed and free portions 152,154 are joined, the arm portion 156 initially extends along a portion of the bottom wall 114 towards the lingual direction, then bends toward the occlusal direction and extends along the first side wall 110, while generally following the overall contour of the archwire slot 108. On the occlusal end of the free portion 154, the arm portion 156 is integrally connected to the head portion 160 that terminates in a location between the reference places 116,118. The head portion 160 at least partially extends across the path of entry for an archwire to be received in the archwire slot 108 from the perspective shown in FIG. 2. Preferably, the occlusal side of the head portion 160 is tapered to facilitate insertion of an archwire as shown. The head portion 160, the arm portion 156, and the fixed portion 152 collectively define an archwire receiving region 158 of each clip 150.

As shown in FIG. 2, each tab 151 extends adjacent to the arm portion 156 of the respective clip 150. To facilitate assembly, each tab 151 has a facial-lingual dimension that generally increases when approaching the head portion 160 of the respective clip 150. Each tab 151 also has an occlusal edge that is coplanar with the bottom wall 114 of the archwire slot 108.

Figure 5:
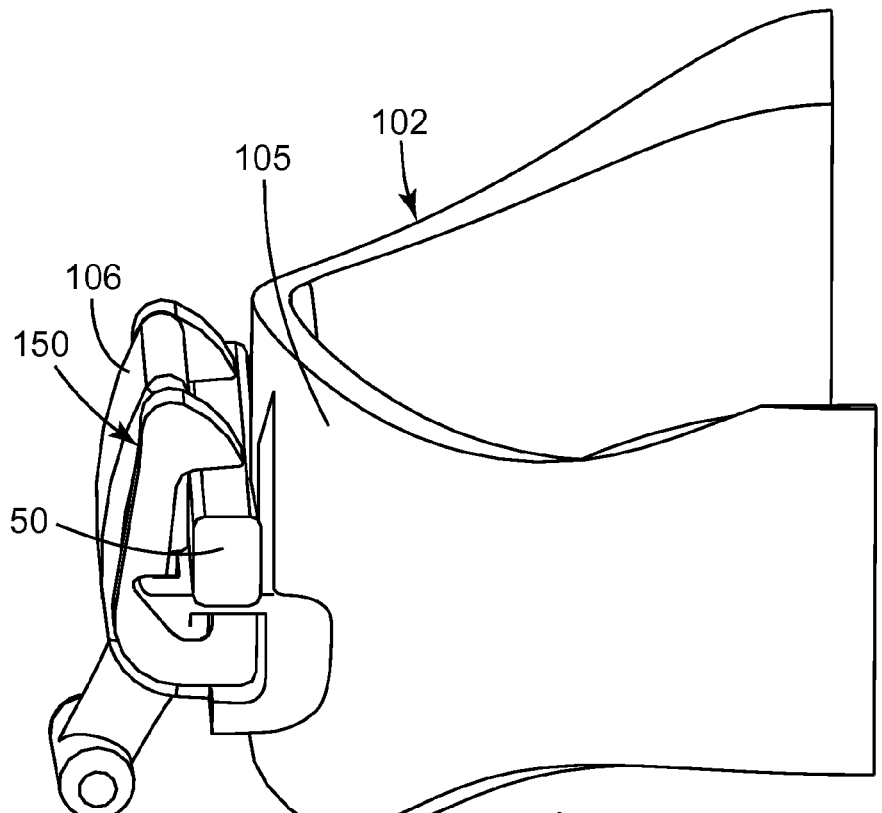
FIG. 5 is a perspective view of the appliance in FIGS. 1-4, including a fragmentary view of an archwire retained in the appliance.

The pair of clips 150 are shown in their normal, relaxed orientation in the drawings. However, the free portions 154 are capable of being deflected away from the second side wall 112 when desired in order to provide an enlarged opening to admit, for example, a rectangular archwire 50 into the archwire slot 108 as shown in FIG. 5. As the archwire 50 is urged toward the bottom wall 114 of the archwire slot 108, the tapered head portions 160 of the clips 150 contact the gingival-lingual corner of the archwire 50. By virtue of the taper of the head portions 160, contact pressure from the archwire 50 causes the clips 150 to simultaneously deflect open toward the lingual direction, allowing the archwire 50 to be fully received into the archwire slot 108.

Once the archwire 50 is received into the archwire slot 108, the inherent resiliency of the clips 150 enables the free portions 154 to spring back toward their normal relaxed or closed configurations as shown in FIGS. 1-5 to retain the archwire 50 in the bracket 100. As particularly illustrated in FIG. 5, the archwire receiving region 158 of each clip 150 is aligned with the archwire slot 108 when the clips 150 are assembled to the body 106. Moreover, the closest distance between each arm portion 156 and the second wall 112 of the archwire slot 108 in facial-lingual directions is greater than the distance between the first and second walls 110,112 of the archwire slot 108, which tends to reduce the resistance to sliding movement between the archwire 50 and the bracket 100 that might otherwise be due to the clips 150.

The insertion of the archwire 50 into the archwire slot 108 as described above may be carried out using finger pressure by the practitioner. Alternatively, the insertion process may be carried out using a suitable orthodontic hand instrument such as a pair of Weingart pliers.

The body 106 also includes a convex ledge 122 adjacent to, and on the lingual side of, the opening to the archwire slot 108. The ledge 122 is precisely shaped to receive a plunger of a hand instrument that is constructed to remove an archwire from the archwire slot 108. The ledge 122 provides structure to align and engage the hand instrument with the bracket 100 during a procedure to release the archwire 50 from the clips 150 and remove the archwire 50 from the archwire slot 108. In an exemplary embodiment, the hand instrument uses a pair of hooks to engage facial surfaces of the archwire 50 on the mesial and distal sides of the bracket 100 and apply a pulling force to disengage the archwire 50, and a concave plunger tip simultaneously applies a reciprocal pushing force against the ledge 122. Other options and advantages of the hand instrument are described in PCT Publication No. WO2010/014299.

As presently preferred, the clips 150 are made from a flat annealed superelastic material (such as nitinol) having a pickled surface. Preferred nitinol materials have a nickel content of 55.97% by weight and an austenite transformation finish temperature ($A_f$) of 10°+/−5° Celsius. The nitinol is cold worked to 37.5% and has a thickness in the range of about 0.012 in. (0.3 mm) to about 0.016 in. (0.4 mm). The clips 150 are first formed in a rough cutting electrical discharge machining (EDM) process, then cut along their edges for an additional one or more times using an EDM process in order to smooth the edges. Alternatively, a laser cutting process or chemical etching process could be used to make the clips 150. Preferably, the clips 150 are constructed so that the longitudinal direction of the clip material, or the principal direction of grain flow of the clip material, is substantially parallel to the direction of extension of the free portions 154 (i.e. in a generally occlusal direction as shown in the illustrated embodiment).

Subsequent to the EDM, laser cutting or chemical etching process, the clips 150 are tumbled in order to further round their edges. An example of a suitable tumbling machine is model LC-600-2+2 from Richwood Industries of Hawthorne, Calif. Using a small barrel, and a machine speed of 200 rpm, the clips are tumbled for about 2 hours in 500 cubic centimeters (cc) of water and tumbling media. An example of suitable tumbling media is a mixture of 500 cc of ceramic media (shaped ACC, type M, size 3/16×3/8 (4.7 mm×9.5 mm)), 25 cc of white alumina powder no. 40, and 25 cc of soap powder compound no. 43, all from Richwood Industries. The tumbled clips are then polished for one-half hour in an ultrasonic screen barrel in a tank of solution. An example of a suitable solution is 3 liters of deionized water, 3 liters of pickling solution and 0.6 liter of hydrogen peroxide. A suitable pickling solution is No. TI121 Pickling Solution from Aya International of Los Angeles, Calif.

The clips 150 should have sufficient flexibility and resilience to deflect open and closed over many cycles with little or no change in engagement or disengagement force. Preferably, each clip 150 has a maximum localized first principal strain of 8% or less when receiving a rectangular archwire having a lateral dimension equivalent to the distance between the side walls of the archwire slot. Maintaining the first principal strain at 8% or less can help preserve the fatigue life of the clips 150.

The bracket 100 has several advantages that provide improved ease of use and patient comfort compared with other self-ligating concepts disclosed in the art. For one, by joining the fixed and free portions 152,154 of the clip 150 in a location between the pair of reference planes 116,118, it is possible to merge a substantial portion of the body with the base 102 of the bracket 100. This in turn lowers the overall profile of the appliance against the patient's tooth, providing additional space for the patient's tongue and thus enhancing patient comfort and lessening speech impediment. The reduction in bracket profile is especially significant in the posterior regions of the dental arch, where the lingual surfaces of the teeth are nearly vertical thereby allowing the archwire slot 108 to be essentially flush with the inner surface 105 of the base 102.

By virtue of having a reduced profile, there is greater flexibility in selecting a bonding site on the surface of the tooth. This is especially beneficial when dealing with the lingual surfaces of the teeth because the amount of space available for a lingual appliance is already constrained by the tongue and neighboring teeth.

The reduced profile of the bracket 100 also provides benefits in treatment. For example, the bracket 100 allows the archwire slot 108 to be moved closer to the lingual surfaces of the respective tooth, which increases inter-bracket spacing and/or mesial-distal bracket width. When dealing with lingual braces, inter-bracket spacing is often quite limited because of the concavity of the lingual side of the dental arch and can limit the mechanical ability of the archwire to move teeth. The bracket 100 provides a greater distance along which an archwire can operate and also facilitates sliding mechanics of the archwire, particularly when the patient's teeth are crowded. If desired, the mesial-distal width of the bracket 100 can be increased to provide improved leverage for tooth movement.

As a further advantage and as shown in FIG. 2, the fixed and free portions 152,154 are joined in a location facial to the contact point between the archwire 50 and the head portion 160. This configuration provides a mechanical advantage whereby a gingival force (i.e. downward force in FIG. 2) applied to the head portion 160 of the clip 150 creates a moment that tends to pivot the free portion 154 about the fixed portion 152 in a counterclockwise direction as depicted in FIG. 2. The resulting pivotal deflection of the free portion 154 assists in opening the clip 150 and reduces the force needed to slip the archwire 50 past the head portion 160 of the clip 150. This configuration also allows strain imposed on the clip 150 to be spread along the entire length of the arm portion 156 which extends the fatigue life of the clip 150 compared with clips that experience greater localized strain in operation.

Figure 6:
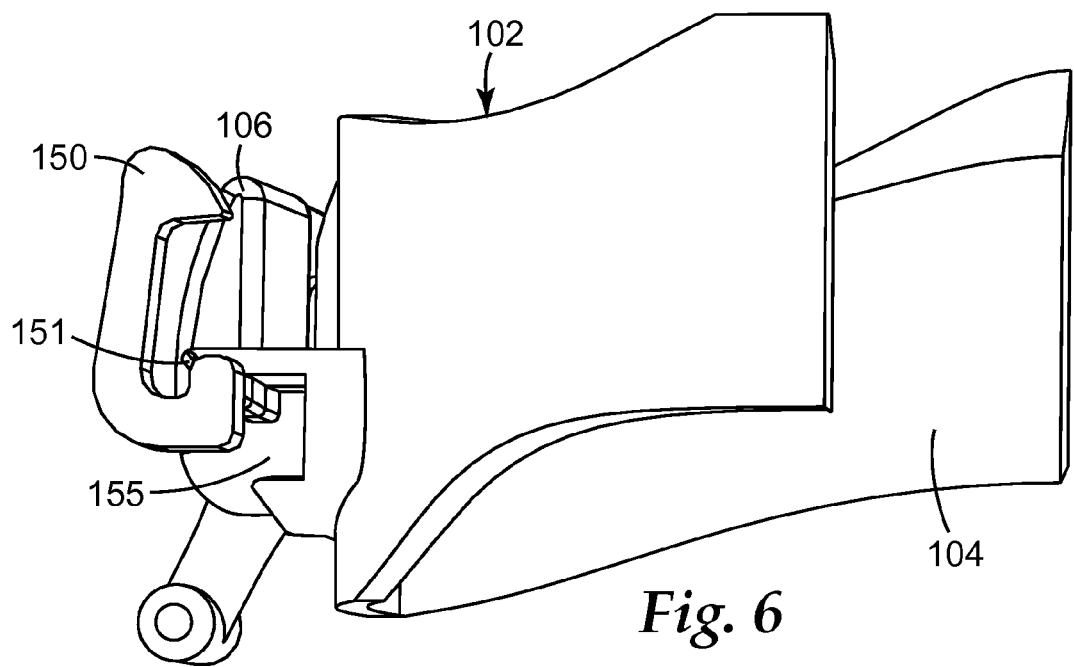
FIG. 6 is a perspective view of the appliance in FIGS. 1-5 in partially assembled form, looking at the facial, mesial, and gingival sides and showing an exemplary method of assembly.

FIG. 6 illustrates an exemplary method of manufacturing the bracket 100. This method begins with providing the bracket body 106 having the archwire slot 108, cavities 155, and other characteristics already described. In some embodiments, the bracket body 106 is constructed from a gold or stainless steel alloy and formed from a bracket body preform using the procedures described in co-pending PCT Application, Serial No. US2009/051790 (Lai et al.), filed on Jul. 26, 2009. Alternatively, the bracket body 106 can be manufactured using a metal injection molding (MIM) process, or using a conventional casting and/or machining process.

The clip 150 is then positioned next to the cavity 155 such that the archwire receiving region 158 is aligned with the archwire slot 108, as shown in FIG. 6. The clip 150 is then subsequently urged toward the cavity 155 to press fit the fixed portion 152 of the clip 150 into the body 106 while simultaneously deflecting the free portion 154 of the clip around the tab 151 located on the body. Optionally, this step is carried out with the assistance of a tool or jig that holds the clip 150 in its open, deflected state while the clip 150 is aligned with the cavity 155. Preferably, the tool then provides a mechanism for the operator to translate the clip 150 directly past the protruding tabs 151 and into the cavity 155. Once the fixed portion 152 of the clip 150 has been fully seated into the cavity 155, the clip 150 relaxes and reverts back to its original closed configuration. By partially extending across the cavity 155, the tab 151 provides an interference fit that retains the clip 150 against the body 106. Optionally and as shown in the assembled bracket view of FIG. 3, there is a small amount of clearance between the tab 151 and the clip 150 allowing the clip 150 to open and close without hindrance.

To complete the assembly, the remaining clip 150 is then coupled to the opposite side of the body 106 using the same method. Advantageously, this method obviates a separate welding or brazing operation or use of an adhesive for coupling the clips 150 to the body 106.

The cavities 155 have certain features that are advantageous in the assembly of the bracket 100. First, and as shown in FIG. 3, each cavity 155 has an opening extending along at least two orthogonal sides of the body 106-in this case, the mesial-lingual sides of the body 106 and the distal-lingual sides of the body 106. Such openings are advantageous because they are enlarged and provide greater tolerance for misalignment between the clip 150 and the body 106 during assembly. Second, the cavities 155 have tapered side walls 157 which present a funneled entrance for the clip 150. The taper in the side walls 157 is further advantageous because it provides greater space when initially positioning the clip 150 for insertion and also acts to guide the clip 150 as it is slidably received into the cavity 155. These aspects of the cavities 155 also provide a more robust manufacturing process by mitigating the effects of dimensional variability and reducing the likelihood of jamming during assembly.

The assembly represented by the clips 150 and the bracket body 106 has a certain orientation relative to the base 102. This orientation is customized to the configuration of the specific tooth of the specific patient. In the illustrated embodiment, the clips 150 and the archwire slot 108 have openings that are aligned with each other, and the orientation of the openings is custom-oriented to the orientation of the base 102. As a result, for any particular appliance, the orientation of the assembly may vary from patient to patient in accordance with the specific configuration of the patient's cuspid tooth and/or of other aspects of the dental structure for the specific patient undergoing treatment.

An another option, one or more brackets can be created on a computer as a combination of three-dimensional virtual objects including a virtual bracket bonding pad and a virtual bracket body retrieved from a library of virtual bracket bodies. The virtual brackets can be represented as a file containing digital shape data that can be exported to a rapid prototype fabrication device. The rapid prototype fabrication device can be used to make models of the brackets which, in turn, are then used to form molds for subsequent casting of the brackets. Using such a system of customized orthodontic brackets and archwires is described in more detail in issued U.S. Pat. No. 6,776,614 (Wiechmann et al.).

FIGS. 7-10 show perspective, mesial, lingual and occlusal views of a self-ligating bracket 200 according to another embodiment. Unlike bracket 100, which is adapted for bonding to a bicuspid tooth, the bracket 200 is adapted for bonding to a lower anterior tooth of a patient. Like the bracket 100, the bracket 200 includes a bracket base 202 having an inner surface 204, a bracket body 206 extending outwardly from the inner surface 204 and having an archwire slot 208, and a pair of clips 250 coupled to the body 206 and aligned with the archwire slot 208.

The bracket 200 differs from the bracket 100 in other respects. The relative orientation of the bracket body 206 with respect to the base 202 is substantially different to accommodate the more gently sloping lingual surfaces of the lower anterior teeth. Further, the bracket 200 includes a wire guide 271 for accommodating a second archwire, which may be used in combination with, or alternatively to, the archwire slot 208. The wire guide 271 serves a similar function to that of the clips 250 and body 206 as it releasably retains an archwire in the bracket 200 during the course of treatment, but operates using a different principle, as described below.

Figure 7:
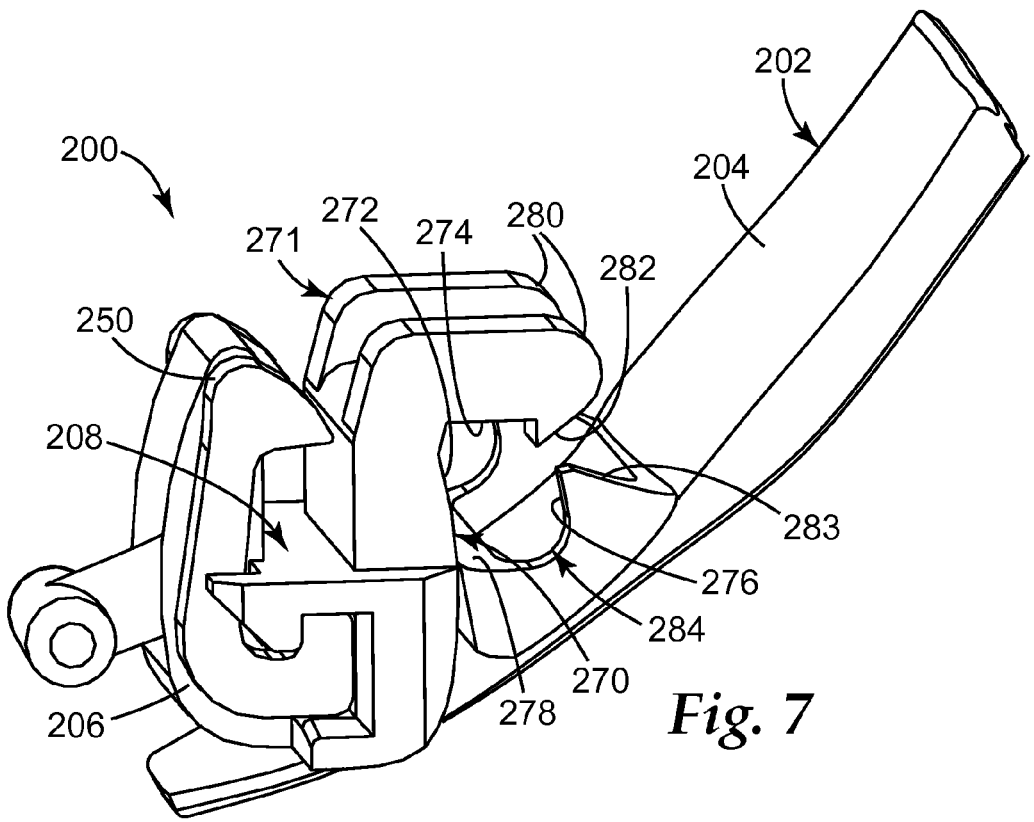
FIG. 7 is a perspective view of a self-ligating orthodontic appliance according to another embodiment, looking at the lingual, mesial, and occlusal sides.
Figure 8:
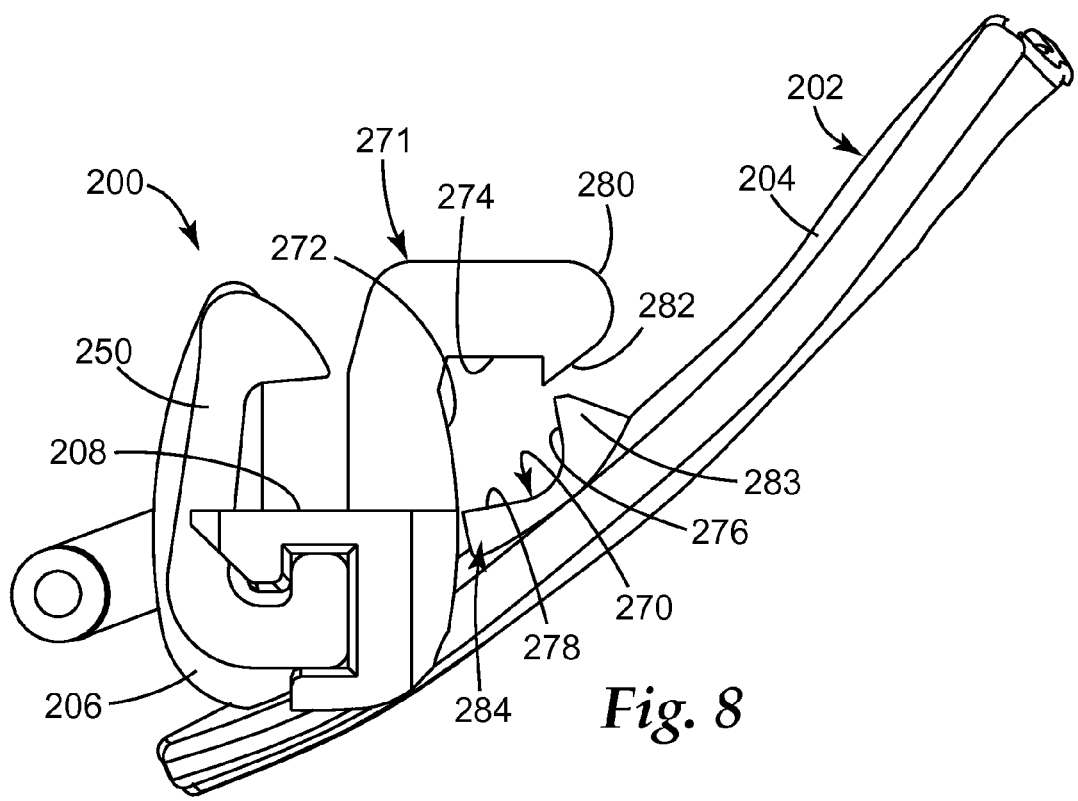
FIG. 8 is a mesial view of the appliance in FIG. 7, looking at the mesial side.
Figure 9:
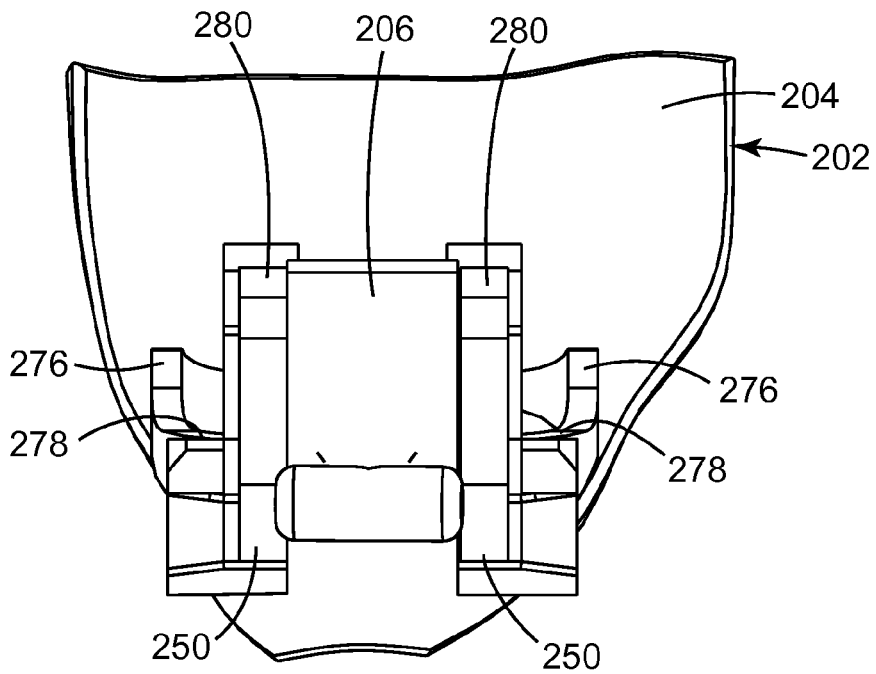
FIG. 9 is a lingual view of the appliance in FIGS. 7-8, looking at the lingual side.
Figure 10:
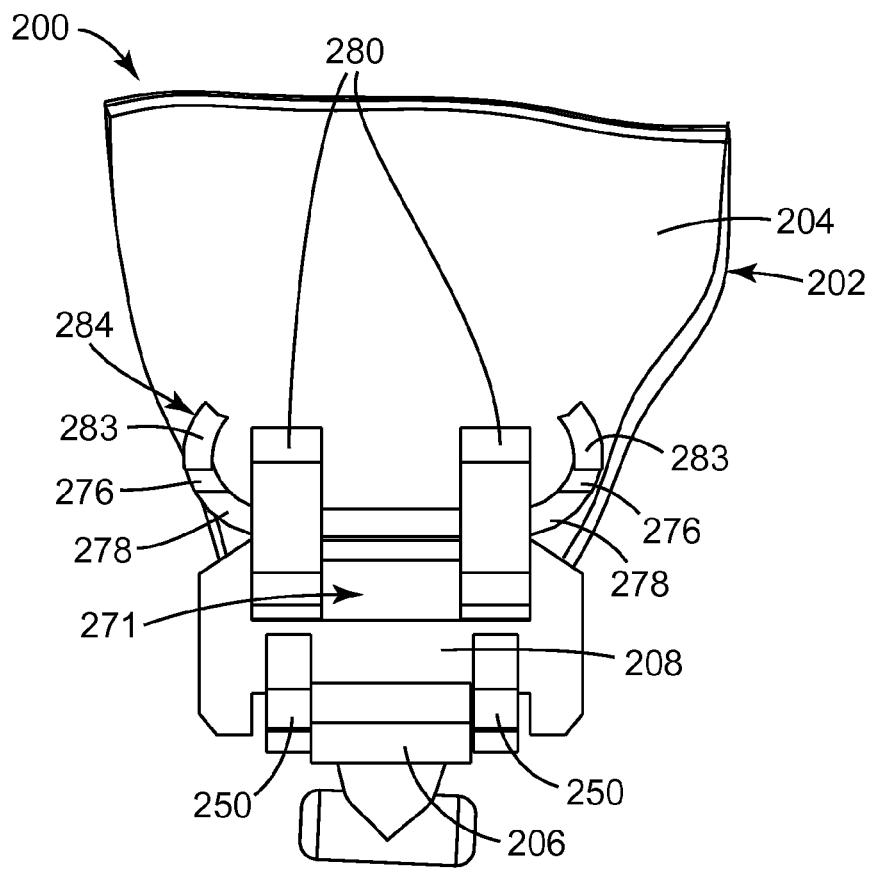
FIG. 10 is an occlusal view of the appliance in FIGS. 7-9, looking at the occlusal side.

As shown in FIGS. 7-8, the wire guide 271 has four inwardly facing wire guide surfaces 272,274,276,278 that face the facial, gingival, lingual, and occlusal directions, respectively. Viewed from the mesial or distal directions, the wire guide surfaces 272,274,276,278 together define a generally rectangular channel 270 for the retention of an archwire. The wire guide surfaces 272,274 are located on each of two inner prongs 280 that extend from the body 106 in a facial direction and terminate in hooks 282. The remaining two wire guide surfaces 276,278 are located on two outer prongs 283 of a shelf member 284, which protrudes from the inner surface 205 of the base 202. While both the outer prongs 283 and the inner prongs 280 surround the channel 270, but the outer prongs 283 are located near the mesial and distal edges of the bracket 200 while the inner prongs 280 are located closer toward the mesial-distal center of the bracket 200, as shown in FIG. 10.

Figure 11:
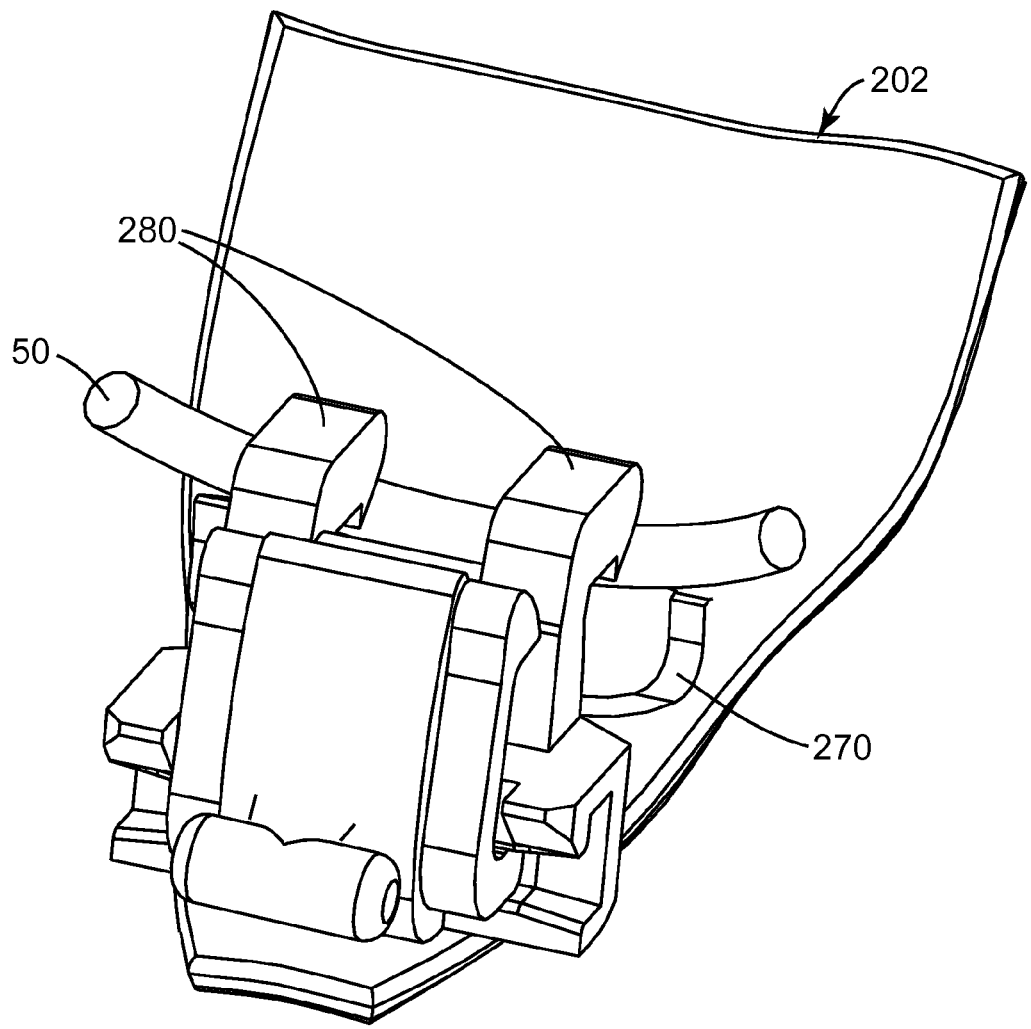
FIG. 11 is another perspective view of the appliance in FIG. 7-10 showing an exemplary method of ligating an archwire in the appliance.

An archwire, such as the archwire 50, is secured into the channel 270 using the procedure illustrated in FIG. 11. First, from the rectilinear state, the archwire 50 is elastically deflected such that the convexity of the archwire 50 between the inner 280 prongs is directed toward the facial direction (into the page as shown in FIG. 11). By virtue of being in this deflected state, the archwire 50 can be guided around the outer prongs 283. Further, the archwire 50 can be simultaneously guided past the protruding hooks 282 of the inner prongs 280 through the free space between the hooks 282 and the inner surface 204 of the base 202. Once the archwire 50 has passed beyond the inner and outer prongs 280,283 and has been received in the channel 270, it reverts back to its original rectilinear state. Back in its rectilinear state, the archwire 50 is now held captive by the wire guide surfaces 272,274,276, 278 located on the inner and outer prongs 280,283. Additional options and advantages of the wire guide 271 are described in PCT Publication No. WO2007/141226 (Wiechmann).

Other characteristics of bracket 200 are similar to those of bracket 100 as already described and need not be repeated.

In previous embodiments, the clip did not exert any compressive force on the archwire once the archwire is retained in the archwire slot of the bracket. This type of coupling is called passive ligation, and can be advantageous where minimal friction is desired between archwire and bracket. However, there are some instances where the practitioner prefers that the clips apply a continuous compressive force against the archwire during the course of treatment. This is known as "active" ligation, results in the archwire being urged toward the bottom wall of the archwire slot and increased resistance to sliding.

Figure 12:
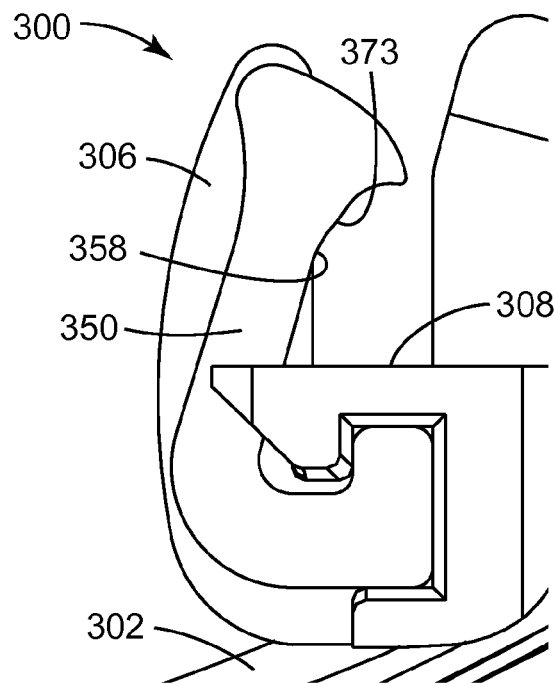
FIG. 12 is an enlarged fragmentary view of an appliance according to still another embodiment.

FIG. 12 shows a self-ligating appliance according to still another embodiment with a clip that provides active ligation. Like the brackets 100,200 earlier described, bracket 300 has base 302 for attachment to a patient's tooth, a bracket body 306 coupled to the base 302, and also a pair of clips 350 coupled to the body 306 in alignment with an archwire slot 308 also located on the body 306. Unlike the clips 150,250 of the brackets 100,200, however, the each of the clips 350 has a bulge 373 that extends into an archwire receiving region 358 of the clip 350.

Figure 13:
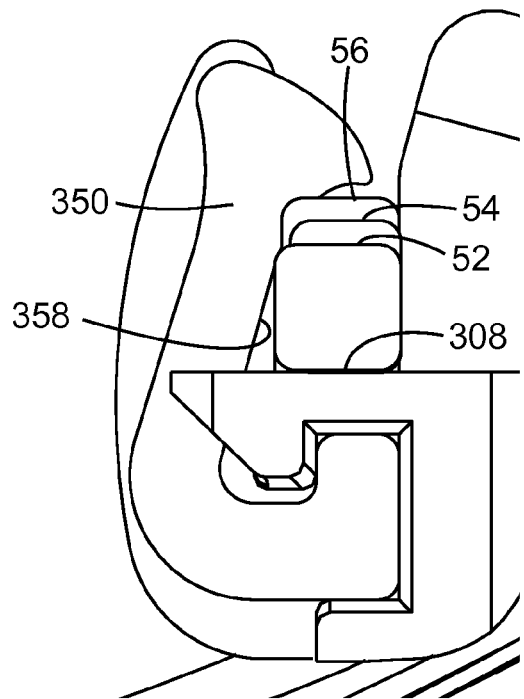
FIG. 13 is the same view shown in FIG. 12, except additionally showing a superposition of three archwires with varying dimensions received in the appliance.
Figure 14:
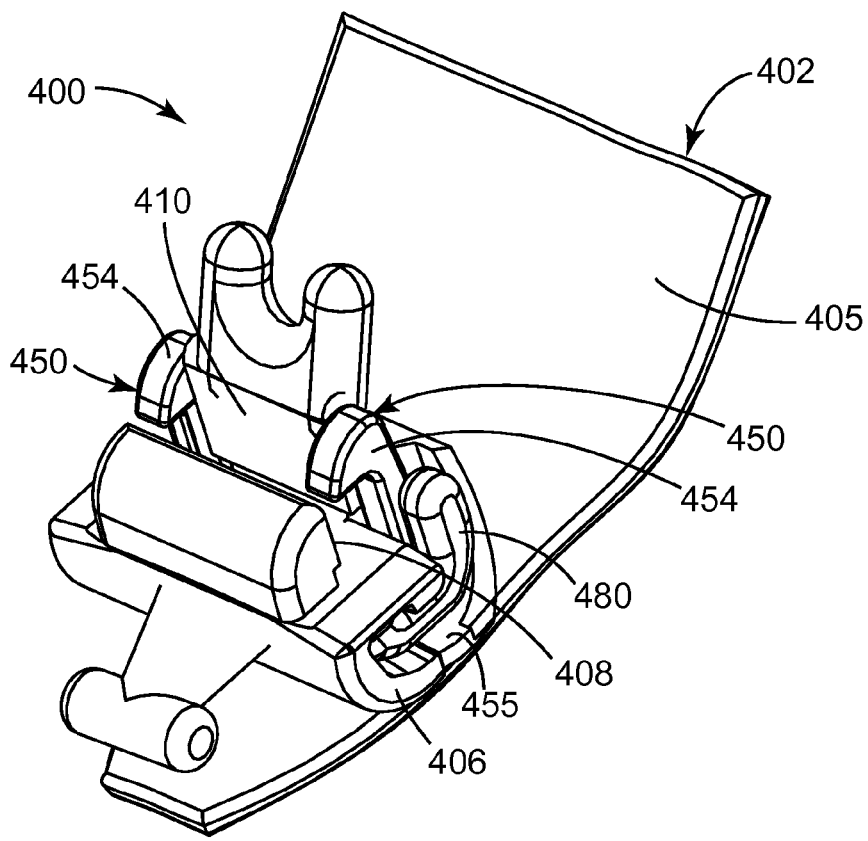
FIG. 14 is a perspective view of a self-ligating orthodontic appliance according to another embodiment, looking at the lingual, mesial, and occlusal sides.
Figure 15:
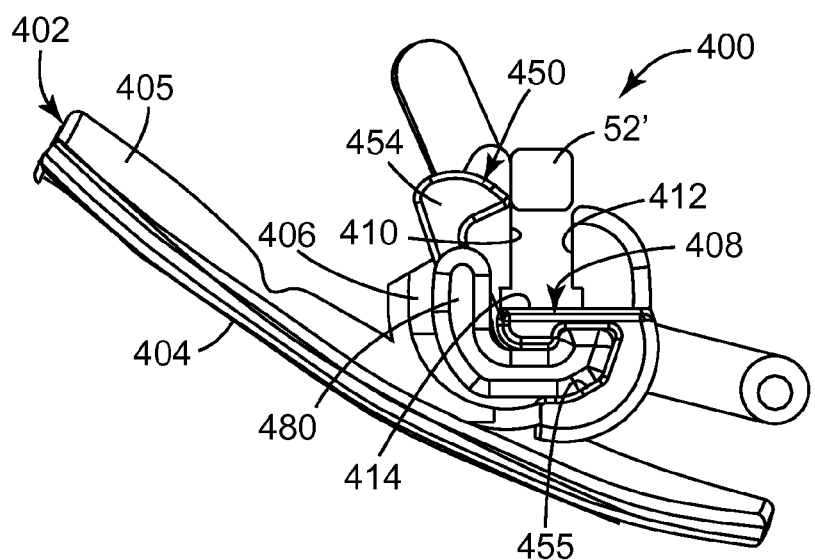
FIG. 15 is a distal view of the appliance in FIG. 14 and an archwire, looking at the distal side and showing an exemplary method of ligation.

The presence of the bulge 373 provides some degree of interference when an archwire of sufficiently large dimensions is received in the archwire receiving region 358 of the clip 350. This is shown in FIG. 13, where three exemplary archwires, a 0.0182 in.×0.0182 in. square archwire 52, a 0.016 in.×0.022 in. rectangular archwire 54 and a 0.017 in.× 0.025 in. rectangular archwire 56, are superimposed within the archwire receiving region 358 of the clip 350 while clip 350 is in a relaxed position. As indicated by the illustrated superposition between the clip 350 and each archwire 52,54, 56, the bulge 373 induces contact between the clip 350 and the archwire 52,54,56 as long as the archwire 52,54,56 is received in archwire slot 308.

FIG. 13 reveals, with respect to the largest archwire 56, there is significant overlap between the archwire 56 and the bulge 373. When the archwire 56 is used, the clip 350 deflects significantly to accommodate the archwire 56 and continuously urges the archwire 56 against the bottom and second side walls of the archwire slot 308 during the course of treatment. As mentioned previously, this results in active ligation and tight engagement between the archwire 52,54,56 and the bracket 300. Such a configuration can provide various advantages to the practitioner. For example, active ligation generally allows increased tip control over the teeth. As another example, active ligation increases sliding friction between the archwire 56 and the bracket 300, which can prevent undesirable tooth movements when making finishing adjustments toward the end of orthodontic treatment. Other aspects of the clips 350 are similar to those of clip 150.

FIGS. 14-26 illustrate several embodiments in which the orientation of the clip is reversed such that the free portion of the clip is positioned on the side of the body nearest to the base.

For example, FIGS. 14-17 show a self-ligating appliance 400 having a base 402 that generally conforms to the lingual surface of a patient's tooth. The base 402 has an outer surface 404 adapted for bonding to the tooth and an inner surface 405. A bracket body 406 extends outwardly from the inner surface 405. The bracket body 406 has an archwire slot 408 extending along a generally mesial-distal direction that includes a first side wall 410 facing generally away from the base 402, a second side wall 412 facing generally toward the base 402, and a bottom wall 414 facing a generally occlusal direction.

As in previous embodiments, a pair of resilient clips 450 are coupled to the mesial and distal sides of the body 406. The clips 450 are planar and have an integral "J"-shaped configuration, with a terminal fixed portion 452 (not visible) rigidly coupled to the body 406 and a free portion 454 that is movable relative to the body 406. However, unlike in previous embodiments, the free portion 454 of each clip 450 is located on the side of the archwire slot 408 adjacent to the base 402 rather than on the side remote from the base 402.

In more detail, each of the fixed portions 452 is rigidly held in a respective complemental cavity 455 set into the body 406. Each of the free portions 454 extend outwardly from the fixed portion 452 along the bottom wall 414 and in a direction generally parallel to the bottom wall 414. Each of the free portions 454 further extends in an occlusal direction along the first side wall 410 and finally terminating beyond the occlusal edge of the second side wall 412 in the occlusal direction when relaxed. No substantial portion of the body 406 adjacent the second side wall 412 protrudes beyond the occlusal edge of the second side wall 412 in the occlusal direction (as used here, a "substantial" portion is one in which such protrusion would interfere with archwire engagement or function as described herein). This clearance presents a path for an archwire 52' (shown in FIG. 15) to engage the free portion 454 of the clip 450 in a direction opposing the first side wall 410 and generally parallel to the bottom wall 414.

The free portion 454 of each clip 450 is joined with its respective fixed portion 452 at a location adjacent the bottom wall 414 and between reference planes defined by the first and second side walls 410 and 412. As in previous embodiments, this aspect is beneficial to the practitioner because it allows the deflection to be spread out along the length of the clip 450, thereby reducing both engagement and disengagement forces. As shown, the body 406 provides adequate clearance for the free portion 454 to deflect in both the occlusal direction (parallel to the side walls 410,412) and the labial direction (perpendicular to the side walls 410,412) as the clip 450 opens to receive the archwire 52'.

Each of the clips 450 is retained against the body 406 by a respective retaining cap 480. Optionally and as shown, each retaining cap 480 is complemental to its cavity 455 and is welded to the mesial and distal sides of the body 406 to prevent the clips 450 from becoming dislodged. In another exemplary mode of assembly, the inner walls of a cavity 455 are slightly tapered. A clip 450 is placed in the cavity 455 such that an archwire receiving region of the clip 450 is aligned with the archwire slot 408. Then, an enlarged broaching tool is forcefully urged into the cavity 455 to permanently deform and fold the inner walls of the cavity 455 toward the clip 450. The deformation of the inner walls provides an interference fit retaining each clip 450 within its respective cavity 455.

Figure 16:
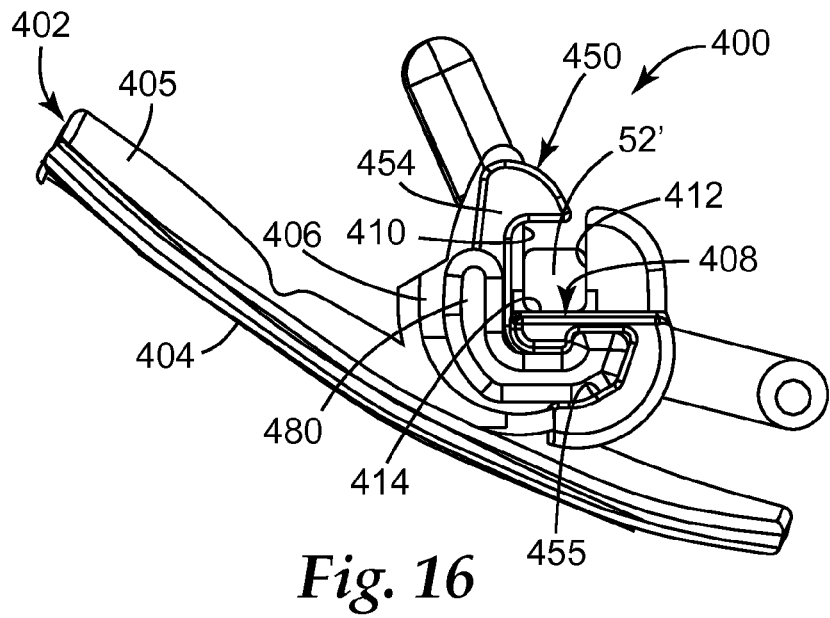
FIG. 16 is a distal view showing the appliance in FIGS. 14-15 and archwire, looking at the distal side.
Figure 17:
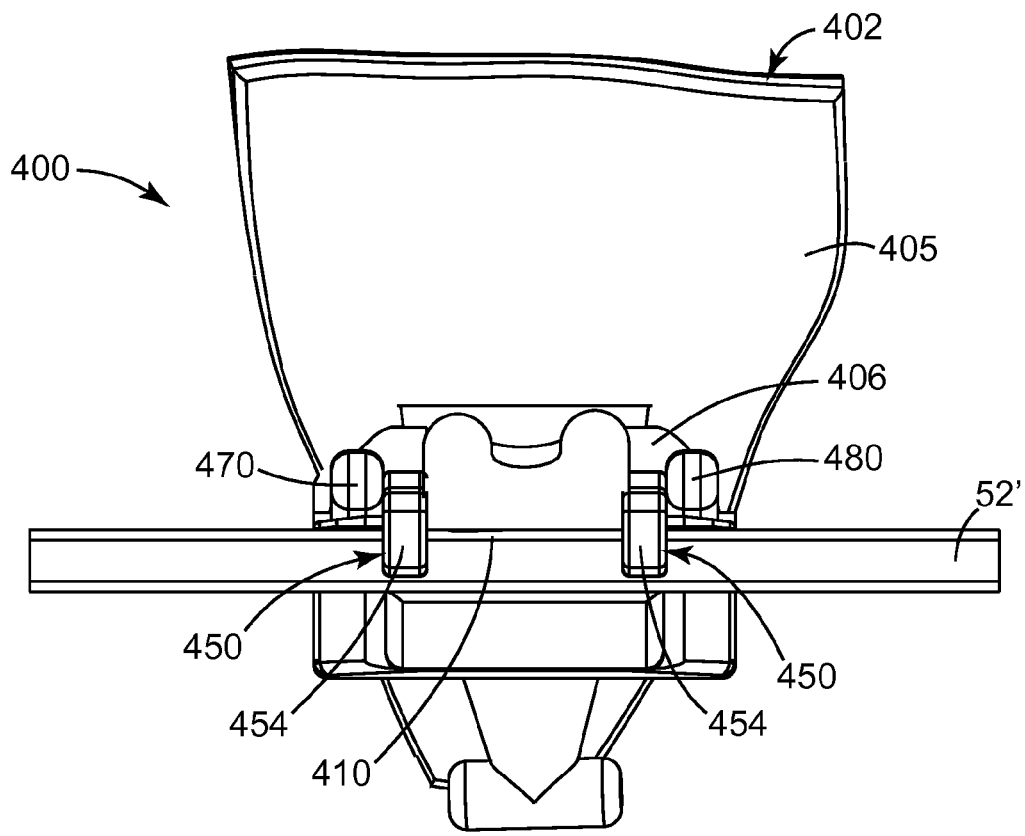
FIG. 17 is an occlusal view of the appliance in FIGS. 14-16, looking at the occlusal side.

The orientation of the clips 450 allows for a novel two-step engagement mechanism. The first step is the opening of the clips 450, shown in FIG. 15. This is accomplished by urging the archwire 52' against the clips 450 in a direction towards the open face of the first side wall 410 and parallel to the bottom wall 414 of the archwire slot 408. As a result, the clips 450 are deflected in the labial direction to provide access to the archwire slot 408. If desired, the archwire 52' can be flatly engaged against the side wall 410 to position the archwire 52' directly over the archwire slot 408. The second step is the sliding movement of the archwire 52' down into the archwire slot 408 along a direction generally parallel to the first side wall 410. FIG. 16 shows the archwire 52' fully seated within the archwire slot 408. Each clip 450 returns toward a relaxed configuration to retain the archwire 52'. Optionally and as shown, the archwire 52' is retained in passive ligation.

The two-step engagement mechanism is advantageous in several respects. First, it effectively decouples archwire alignment and engagement. Alignment is facilitated because the archwire 52' can be aligned against the first side wall 410 from a wide range of directions. Engagement is also facilitated because the archwire can slide directly into the slot once the clips 450 have been opened. Overall, ligation is significantly easier and less technique-sensitive with respect to the practitioner. Second, the acute angle of approach results in an overall decrease in the amount of force required to open the clips 450. This increases the patient comfort during archwire engagement. Third, the configuration of the appliance allows the second side wall 412 to be made significantly shorter, allowing for a lower profile bracket body 406 that provides greater comfort for the patient.

Although not shown, the appliance 700 could also be adapted to allow labial or lingual archwire engagement. For example, the archwire slot opening could face a labial-lingual direction, where the labial/lingual edge of the clip terminates beyond the edge of the second side wall in a labial/lingual direction when relaxed.

Figure 18:
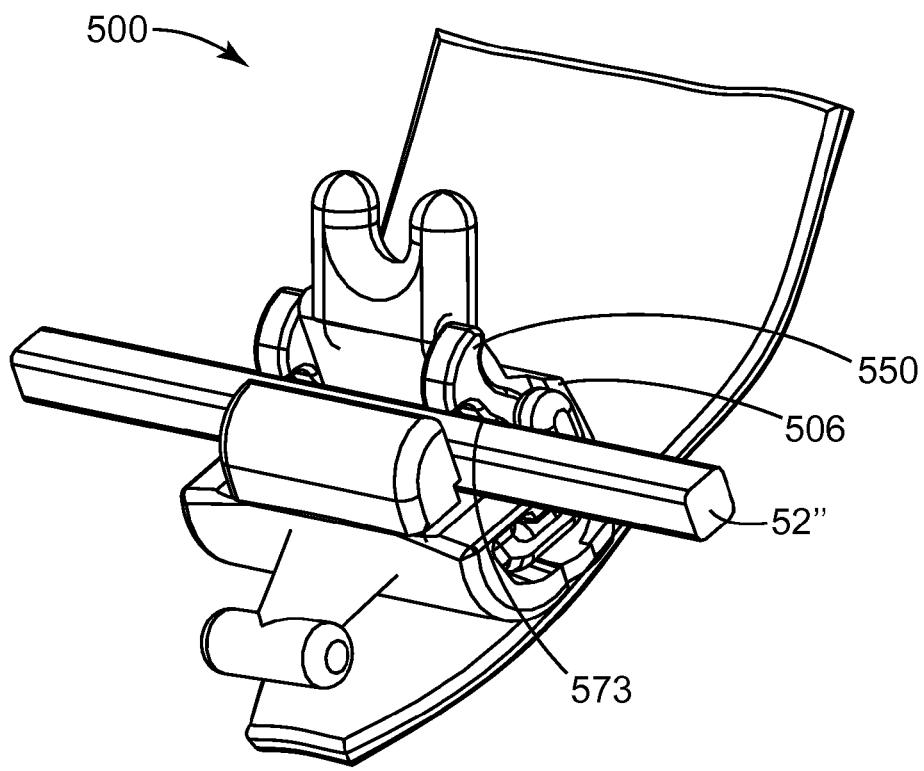
FIG. 18 is a perspective view of a self-ligating orthodontic appliance and an archwire according to another embodiment, looking at the lingual, mesial, and occlusal sides.
Figure 19:
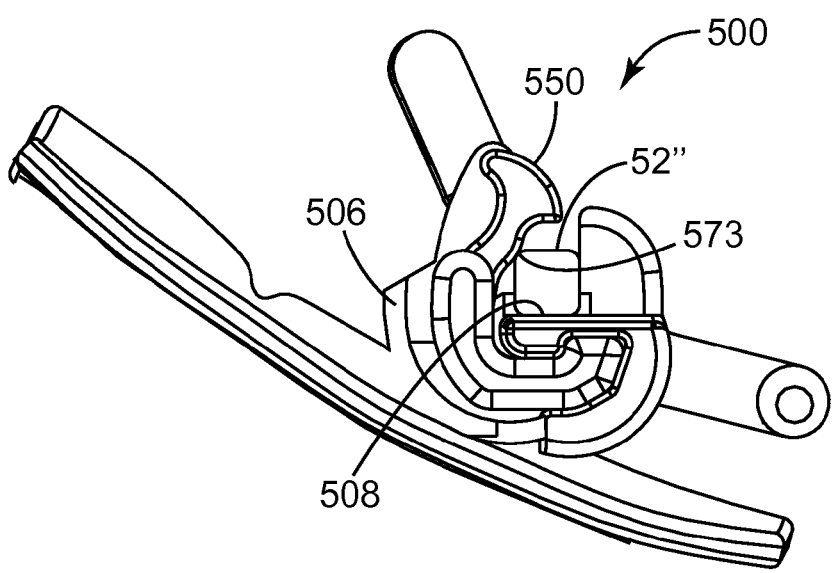
FIG. 19 is a distal view showing the appliance in FIG. 18 and archwire, looking at the distal side.
Figure 20:
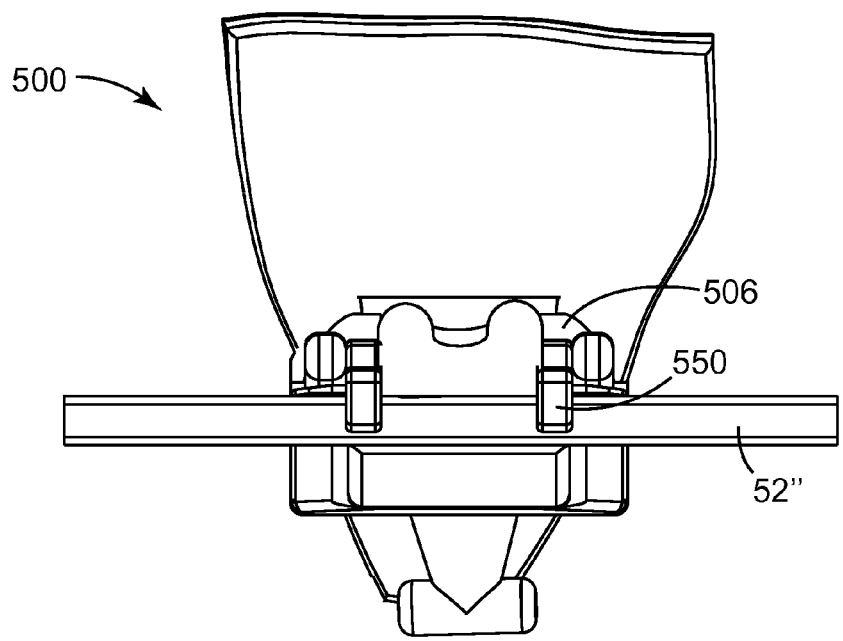
FIG. 20 is an occlusal view of the appliance in FIGS. 18-19 and archwire, looking at the occlusal side.

FIGS. 18-20 show a self-ligating appliance 500 according to a somewhat modified embodiment. The appliance 500 has a bracket body 506 with an archwire slot 508, along with a pair of clips 550. In this embodiment, each of the clips 550 has a convex inner contour, or bulge 573, that extends inward toward the archwire slot 508. Like the bulge 373 of FIG. 12, the bulge 573 provides for an active ligation mechanism that continuously applies a compressive force against an archwire 52''. As previously indicated, active ligation can give a practitioner increased control over the teeth during orthodontic treatment. Additional aspects, options, and advantages of appliance 500 are similar to those described for previous embodiments and will not be repeated.

Figure 21:
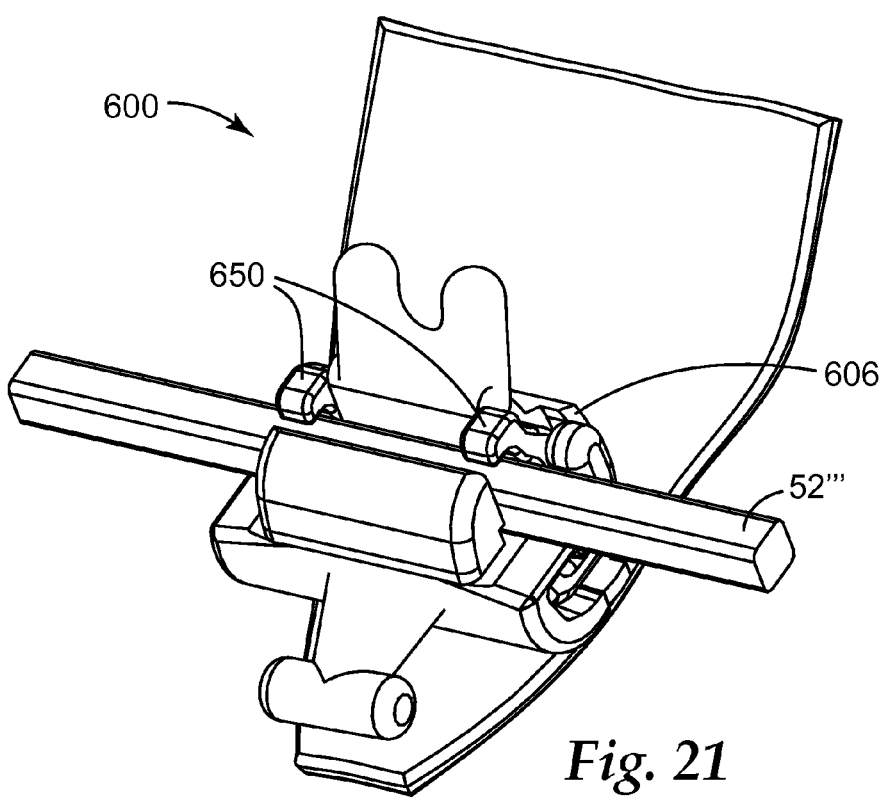
FIG. 21 is a perspective view of a self-ligating orthodontic appliance and an archwire according to another embodiment, looking at the lingual, mesial, and occlusal sides.
Figure 22:
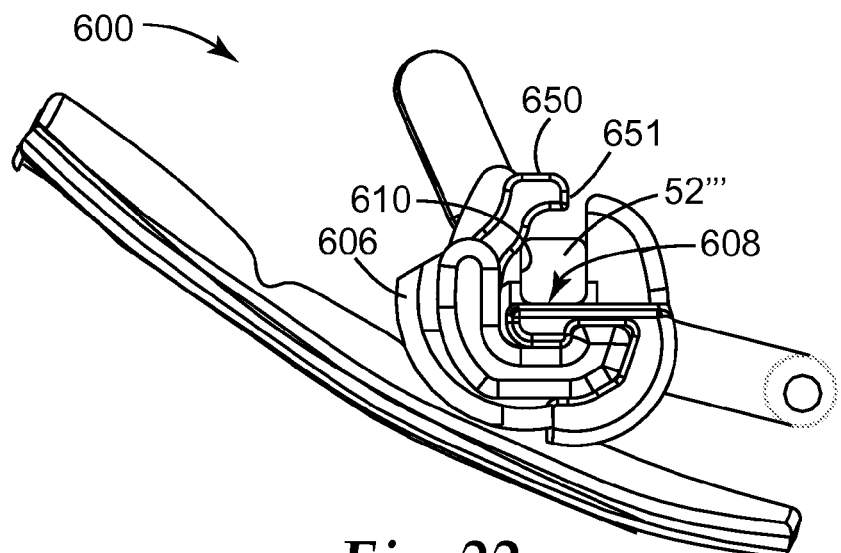
FIG. 22 is a distal view showing the appliance in FIG. 21 and archwire, looking at the distal side.
Figure 23:
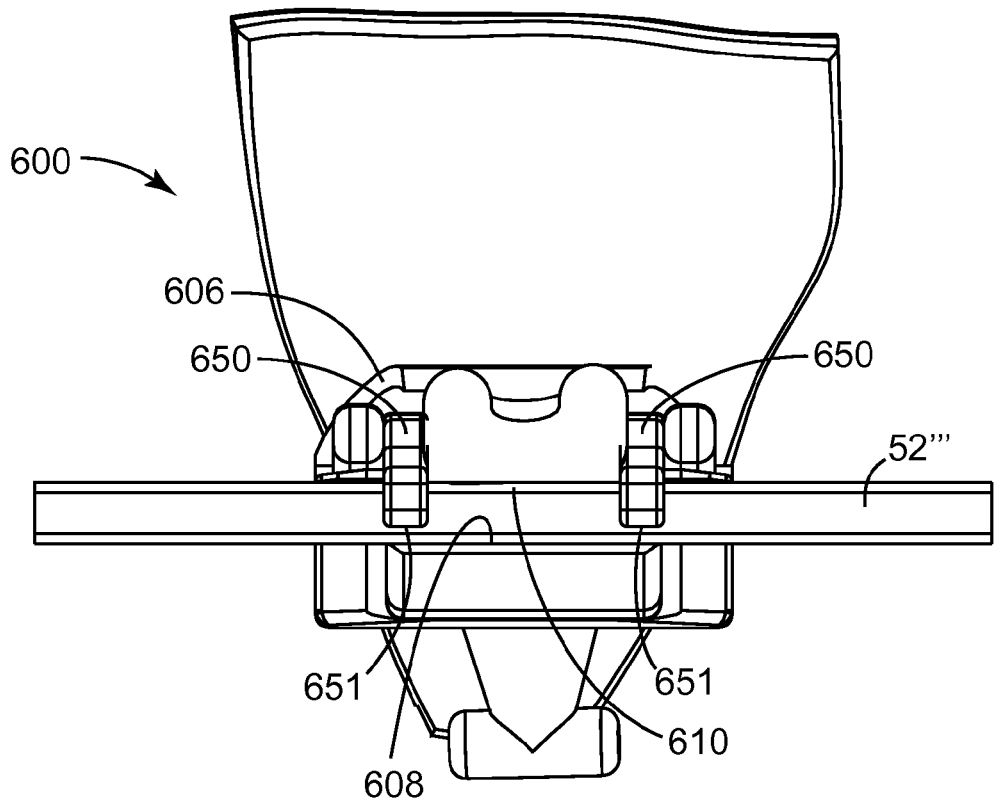
FIG. 23 is an occlusal view of the appliance in FIGS. 21-22 and archwire, looking at the occlusal side.

FIGS. 21-23 show a self-ligating appliance 600 according to another modified embodiment. The appliance 600 has a bracket body 606 with an archwire slot 608 and is coupled to pair of clips 650 aligned with the archwire slot 608. Unlike in previous embodiments, however, each clip 650 has a head portion with a flat surface 651 as shown in FIG. 22. The flat surfaces 651 are generally parallel to the side wall 610 and allow an archwire 52''' to flatly engage one or both clips 650 when aligning the archwire 52''' over the archwire slot 608. A flat engagement surface is beneficial because it presents the practitioner with a wide area for engagement and reduces the likelihood of slippage between the archwire 52''' and the clips 650. Other aspects of appliance 600 are similar to those described for previous embodiments.

Figure 24:
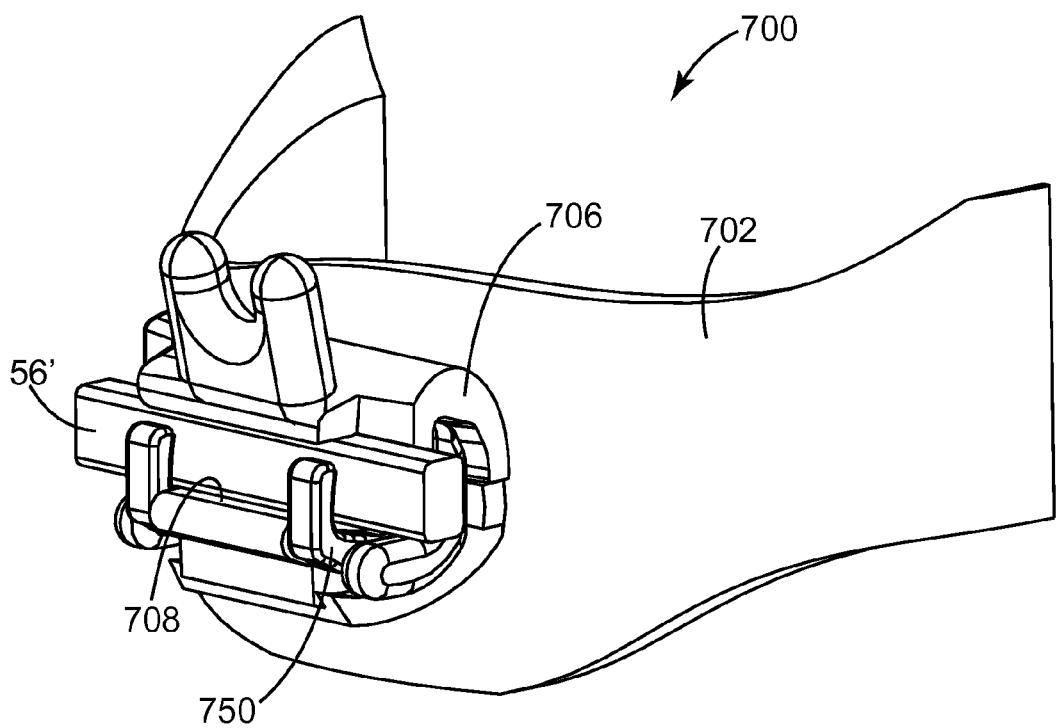
FIG. 24 is a perspective view of a self-ligating orthodontic appliance and an archwire according to another embodiment, looking at the lingual, mesial, and occlusal sides.
Figure 25:
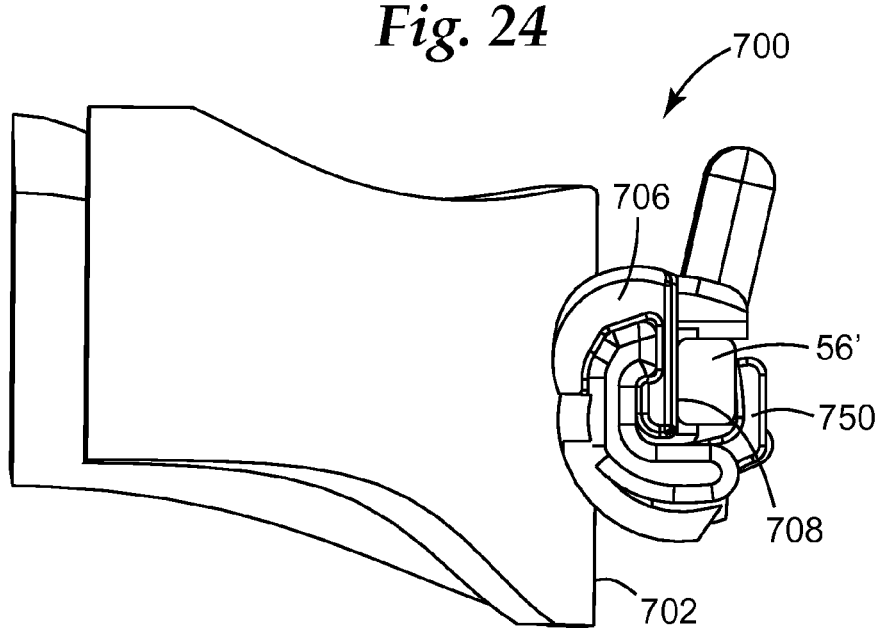
FIG. 25 is a distal view showing the appliance in FIG. 21 and archwire, looking at the distal side.
Figure 26:
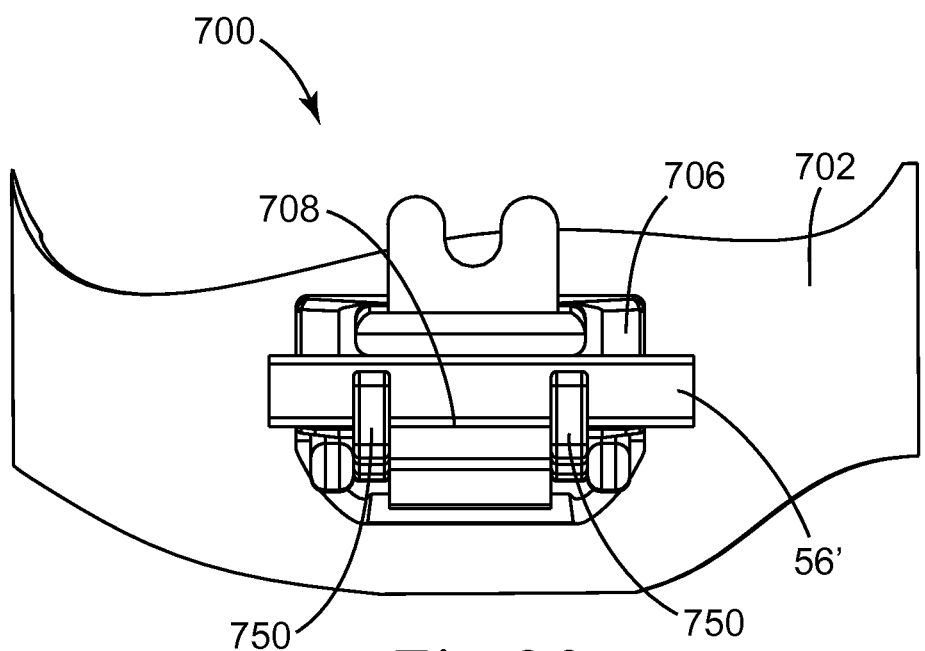
FIG. 26 is a lingual view of the appliance in FIGS. 21-22 and archwire, looking at the lingual side.

FIGS. 24-26 show a self-ligating appliance 700 according to still another embodiment that is directed for use on the lingual surface of a posterior tooth. This appliance 700 has a base 702 and a generally elliptical body 706, as viewed from a mesial-distal direction and shown in FIG. 25. The body 706 has an archwire slot 708, and coupled to the body 706 is a pair of clips 750 aligned with the archwire slot 708. Unlike in previous embodiments, the archwire slot 708 is located on the lingual side of the body 706 and has an opening facing in a generally facial direction (toward the cheek or lips). An exemplary archwire 56' is received in the archwire slot 708 as shown. Other aspects of the appliance 700 are similar to those described for previous embodiments.

All of the patents and patent applications mentioned above are hereby expressly incorporated by reference. The embodiments described above are illustrative of the present invention and other constructions are also possible. Accordingly, the present invention should not be deemed limited to the embodiments described in detail above and shown in the accompanying drawings, but instead only by a fair scope of the claims that follow along with their equivalents.

The invention claimed is:

1. A self-ligating orthodontic appliance comprising:
   a base having an outer surface for attachment to a tooth and an inner surface;

a body extending outwardly from the inner surface, the body including a pair of side walls and a bottom wall extending between the side walls in a direction generally perpendicular thereto, wherein the side walls and the bottom wall define an archwire slot extending in a generally mesial-distal direction;

a cavity extending into the body; and at least one resilient clip adjacent the body for releasably retaining an archwire in the archwire slot, the clip comprising a fixed portion rigidly coupled to the body; and a free portion extending outwardly from the fixed portion along a path parallel to the bottom wall, wherein the pair of side walls defines a pair of reference planes and the fixed and free portions join each other in a location between the reference planes, wherein at least the fixed portion of the clip is received in the cavity, the cavity having a shape that is complemental to at least a portion of the shape of the clip.

2. The appliance of claim 1, wherein one of the pair of side walls is coplanar with at least a portion of the inner surface.

3. The appliance of claim 1, wherein the clip is planar and has a generally "J"-shaped configuration.

4. The appliance of claim 1, wherein the fixed portion and free portion of the clip are integral with each other.

5. The appliance of claim 1, wherein the free portion of the clip further comprises an arm portion extending along one of the pair of side walls and a head portion at least partially extending across the path of entry for the archwire to be received in the archwire slot.

6. The appliance of claim 1, wherein the cavity extends into the body in a generally mesial-distal direction.

7. The appliance of claim 6, wherein the body includes at least two orthogonal sides and the cavity has an opening extending along the at least two orthogonal sides of the body.

8. The appliance of claim 6, wherein the cavity has one or more corner regions that constrain movement of the fixed portion within the cavity.

9. he appliance of claim 6, further comprising a retaining tab protruding from the body and at least partially extending across the cavity, whereby the fixed portion of the clip is held captive by an interference fit.

10. The appliance of claim 9, wherein the retaining tab is adjacent to the arm portion of the clip and has a facial-lingual dimension that generally increases when approaching the head portion of the clip.

11. The appliance of claim 9, wherein the retaining tab has an occlusal edge that is generally coplanar with the bottom wall of the archwire slot.

12. The appliance of claim 1, wherein the clip comprises an active clip applying a continuous compressive force against the archwire during the course of treatment.

13. The appliance of claim 1, wherein the cavity includes side walls that are tapered to present a funneled entrance for the clip.

14. The appliance of claim 1, wherein the clip intersects exactly one of the pair of reference planes.

15. The appliance of claim 1, wherein the clip has a maximum first principal strain of 8% or less when receiving an archwire having a lateral dimension equivalent to the distance between the side walls of the archwire slot.

16. A self-ligating orthodontic appliance comprising:

a base having an outer surface for attachment to a tooth and an inner surface;

a body extending outwardly from the inner surface, the body including a pair of spaced-apart side walls and a bottom wall defining an archwire slot with a slot opening, the archwire slot and the slot opening extending in a generally mesial-distal direction, and wherein the side walls extend in respective reference planes that are generally parallel to each other; and at least one resilient clip adjacent the body for releasably retaining an archwire in the archwire slot, the clip comprising a fixed portion secured to the body in a location adjacent the bottom wall and a free portion extending along a portion of the bottom wall, one of the side walls and the slot opening, wherein the free portion includes a head portion that terminates in a location between the reference planes, wherein the fixed and free portions join each other in a location between the reference planes, and wherein the clip intersects exactly one of the pair of reference planes.

17. The orthodontic appliance of claim 16, wherein the clip is secured to the body by at least one of a press fit or a cap.

18. A method of assembling an orthodontic appliance comprising:

providing a resilient clip having an archwire receiving region;

providing a body having an archwire slot extending across one side of the body, a cavity complemental to at least a portion of the clip, and a tab partially extending across the cavity;

positioning the clip next to the cavity such that the archwire receiving region is aligned with the archwire slot;

urging the clip toward the cavity to press fit a portion of the clip into the body while deflecting another portion of the clip around the tab, wherein the tab provides an interference fit to retain the clip against the body when the clip returns toward a relaxed configuration.

19. The method of claim 18, wherein the cavity extends into the body along a generally mesial-distal direction.

20. The method of claim 18, wherein the cavity includes side walls that are tapered to present a funneled entrance for the clip.

* * * * *

UNITED STATES PATENT AND TRADEMARK OFFICE
CERTIFICATE OF CORRECTION

| | |
|---|---|
| PATENT NO. | : 8,827,698 B2 |
| APPLICATION NO. | : 13/498408 |
| DATED | : September 9, 2014 |
| INVENTOR(S) | : Ming-Lai Lai |

It is certified that error appears in the above-identified patent and that said Letters Patent is hereby corrected as shown below:

In The Claims

Column 15
Line 40 (Approx.), in Claim 9, delete "he" and insert -- The --, therefor.

Signed and Sealed this
Twenty-third Day of June, 2015

Michelle K. Lee
*Director of the United States Patent and Trademark Office*